United States Patent [19]

Meltzer

[11] Patent Number: 5,591,211
[45] Date of Patent: Jan. 7, 1997

[54] DEFIBRILLATOR HAVING REDUNDANT SWITCHABLE HIGH VOLTAGE CAPACITORS

[75] Inventor: Mark J. Meltzer, San Francisco, Calif.

[73] Assignee: Ventritex, Inc., Sunnyvale, Calif.

[21] Appl. No.: 353,406

[22] Filed: Dec. 9, 1994

[51] Int. Cl.$^6$ ............................................. A61N 1/39
[52] U.S. Cl. ..................................... 607/5; 607/34
[58] Field of Search ............... 607/4, 5, 7, 11, 607/15, 17, 9, 14, 8, 29, 34

[56] References Cited

U.S. PATENT DOCUMENTS

| | | | |
|---|---|---|---|
| 4,254,775 | 3/1981 | Langer et al. | 128/419 |
| 5,111,816 | 5/1992 | Pless et al. | 128/419 |
| 5,199,429 | 4/1993 | Kroll et al. | 607/5 |
| 5,230,712 | 7/1993 | Matthews | 29/25.03 |
| 5,279,293 | 1/1994 | Andersen et al. | 607/2 |
| 5,330,509 | 7/1994 | Kroll et al. | 607/14 |
| 5,350,405 | 9/1994 | Silvian | 607/11 |
| 5,385,575 | 1/1995 | Adams | 607/15 |
| 5,395,395 | 3/1995 | Hedberg | 607/7 |
| 5,449,377 | 9/1995 | Adams et al. | 607/7 |
| 5,453,698 | 9/1995 | Williams et al. | 607/5 |
| 5,458,624 | 10/1995 | Renirie et al. | 607/20 |
| 5,488,553 | 1/1996 | Renger | 607/7 |

FOREIGN PATENT DOCUMENTS

| | | | |
|---|---|---|---|
| 0599588 | 6/1994 | European Pat. Off. | 607/5 |
| 9421327 | 9/1994 | WIPO | 607/5 |

OTHER PUBLICATIONS

"Implantable Cardioverters and Defibrillators", Paul J. Troup, M.D., *Current Problems in Cardiology*, Dec. 1989, pp. 704–713.

*Primary Examiner*—William E. Kamm
*Assistant Examiner*—George R. Evanisko
*Attorney, Agent, or Firm*—Steven M. Mitchell; Mark J. Meltzer

[57] ABSTRACT

An implantable cardioverter defibrillator having a plurality of high voltage capacitors in the output stage which are coupled in parallel and a switching matrix for controlling the number of capacitors used to deliver the shock. For patients having lower DFTs, the number of capacitors in the output stage, as controlled by the switching matrix, can be reduced thus reducing the capacitor charging time prior to delivering a defibrillation shock. Additionally, if one of the capacitors experiences a degradation in performance, it can be switched out of the output circuit as long as the remaining capacitors can provide the necessary energy delivery for defibrillation. In another embodiment of the invention, if a particular defibrillation shock is ineffective, the back-up capacitors may be switched into the high voltage output circuit for delivery of the next shock.

4 Claims, 2 Drawing Sheets

DEFIBRILLATOR HAVING REDUNDANT SWITCHABLE HIGH VOLTAGE CAPACITORS

BACKGROUND OF THE INVENTION

1. Technical Field

The invention relates generally to implantable medical devices. More particularly, the invention relates to an implantable cardiac defibrillator that provides the ability to control the capacitance of the high voltage output stage.

2. Description of the Prior Art

The use of implantable cardioverter/defibrillators (ICDs) to treat cardiac tachyarrhythmias is well known in the prior art. Advances in microelectronics and microprocessors have allowed for reduction in the size and weight of such ICDs, and for the use of more sophisticated techniques in the detection and treatment of such arrhythmias. The two current primary limiting factors in the reduction in size of ICDs are the high voltage capacitors and the batteries. A higher energy density, and thus smaller, capacitor design is disclosed in U.S. Pat. No. 5,230,712 "Method for Producing Multi-Cell Solid State Electrochemical Capacitors and Articles Formed Thereby" to Matthews, which is incorporated herein by reference. Such capacitors allow for output stage high voltage capacitor configurations which have not previously been practical.

Kroll, et al, "Method and Apparatus for Far-Field Tachycardia Termination", U.S. Pat. No. 5,330,509, discusses a two-capacitor system within the context of far-field cardiac stimulation. Kroll discloses the use of a second capacitor to deliver the far-field stimulation pulses, in addition to the pulses provided by the primary capacitor. The defibrillation device, while using two capacitors, does not have the ability to selectively use one or both capacitors for the delivery of a single pulse. Further, the secondary capacitor does not function as a back-up to replace a malfunctioning primary capacitor.

As ICDs are used to treat an expanding variety of arrhythmias, the consequences of an ICD failure are of increasing significance. One of the components of an ICD that has a low, but real, possibility of failure is the high voltage capacitors of the output stage. Current systems monitor capacitor charge times to allow identification of a degraded capacitor. It would be a significant advance in the art to provide an implantable cardiac defibrillator which could replace a substandard capacitor with a back-up capacitor. Current practice is to remove and replace an ICD if there has been an HV capacitor degradation or failure. Because of this, very expensive capacitors are used in ICDs and they are subjected to extensive quality control testing to ensure that there is no failure. However, such extreme measures might not be necessary in a system having backup or redundant capacitors, since redundant, standard off-the-shelf capacitors might actually provide a higher system reliability than is provided by a single super-premium capacitor.

An additional issue associated with the HV capacitors of an ICD is the amount of time it takes to charge the capacitors. The charge time is typically about 10 to 15 seconds and is governed by the formula $$V=V_{app}(1-\exp(-t/RC))$$

where V is the target voltage, $V_{app}$ is the applied voltage, R is the effective resistance of the capacitor and C is the capacitance of the capacitor. It can be seen that the charging time is directly proportional to the capacitance. Since it has been found that defibrillation shocks are most effective when delivered as quickly as possible following the detection of fibrillation, the shorter the charge time for the capacitors the more effective the defibrillation therapy.

For each patient receiving an ICD, the surgeon performs a series of tests at the time of implant to determine the defibrillation threshold (DFT) for that patient. The DFT is a measure of the minimum energy required to defibrillate that patient's heart. This value may vary significantly from patient to patient and may change over time for a given patient. Once the DFT is determined, the ICD is programmed to deliver defibrillation shocks of an energy with a safety margin above the DFT. The energy stored by the HV capacitors is a function of the capacitance and voltage according to the formula $$E=\tfrac{1}{2}CV^2$$

A significant fraction of this energy from a charged capacitor is delivered to the patient depending on the programmed time duration of the shock. Prior art systems have a fixed capacitance and thus, for a given energy delivery requirement, the voltage to which the capacitors are charged controls the energy in the shock delivered to the patient and this energy is a linear function of the capacitance of the capacitor. The charge time for the HV capacitors is thus fixed for a given final voltage (assuming a constant battery supply voltage.) It would be advantageous to provide a system allowing a reduced charge time for the HV capacitors in cases where the patient's DFT is low enough so that it isn't necessary to utilize the total available system capacitance to deliver sufficient defibrillation energy to the heart.

A typical operational sequence to which an ICD may be programmed is to provide a first defibrillation shock at 500 volts, a second shock at 700 volts if the first shock fails to defibrillate the heart and then two additional shocks at 750 volts if the preceding shock in ineffective. Each of the increases in voltage significantly increases the energy delivered since the energy is a function of the square of the voltage. However, in some cases these shocks still do not defibrillate the heart. It would be beneficial to have a way to provide additional energy delivery capability in the event of failure of the programmed shock sequence to effect defibrillation.

It is therefore an object of the invention to provide an ICD with a high voltage output stage having a selectively variable capacitance.

It is a further object of the invention to provide an ICD with back-up high voltage capacitors to replace degraded capacitors.

It is another object of the invention to provide an ICD wherein back-up high voltage capacitors are used to provide a maximum energy defibrillation shock in the event lower energy shocks fail to defibrillate the heart.

SUMMARY OF THE INVENTION

The invention provides an implantable cardioverter defibrillator (ICD) having a plurality of high voltage (HV) capacitors in the output stage which are coupled in parallel and a switching matrix used to control the number of capacitors used to deliver a defibrillation shock. For patients having lower DFTs, the number of capacitors in the output stage, as controlled by the switching matrix, can be reduced thus reducing the charging time. Further, with this system, if one of the capacitors in the output stage experiences a degradation in performance, it can be switched out of the output circuit as long as the remaining capacitors provide the necessary energy delivery for the given patient.

In another embodiment of the invention, if a particular defibrillation shock is ineffective, the back-up capacitors may be switched into the high voltage output circuit for delivery of the next shock. This may be done at the initial shock voltage before increasing the voltage or it may done after the highest voltage shock is delivered and is ineffective.

DETAILED DESCRIPTION OF THE INVENTION

Figure 1:
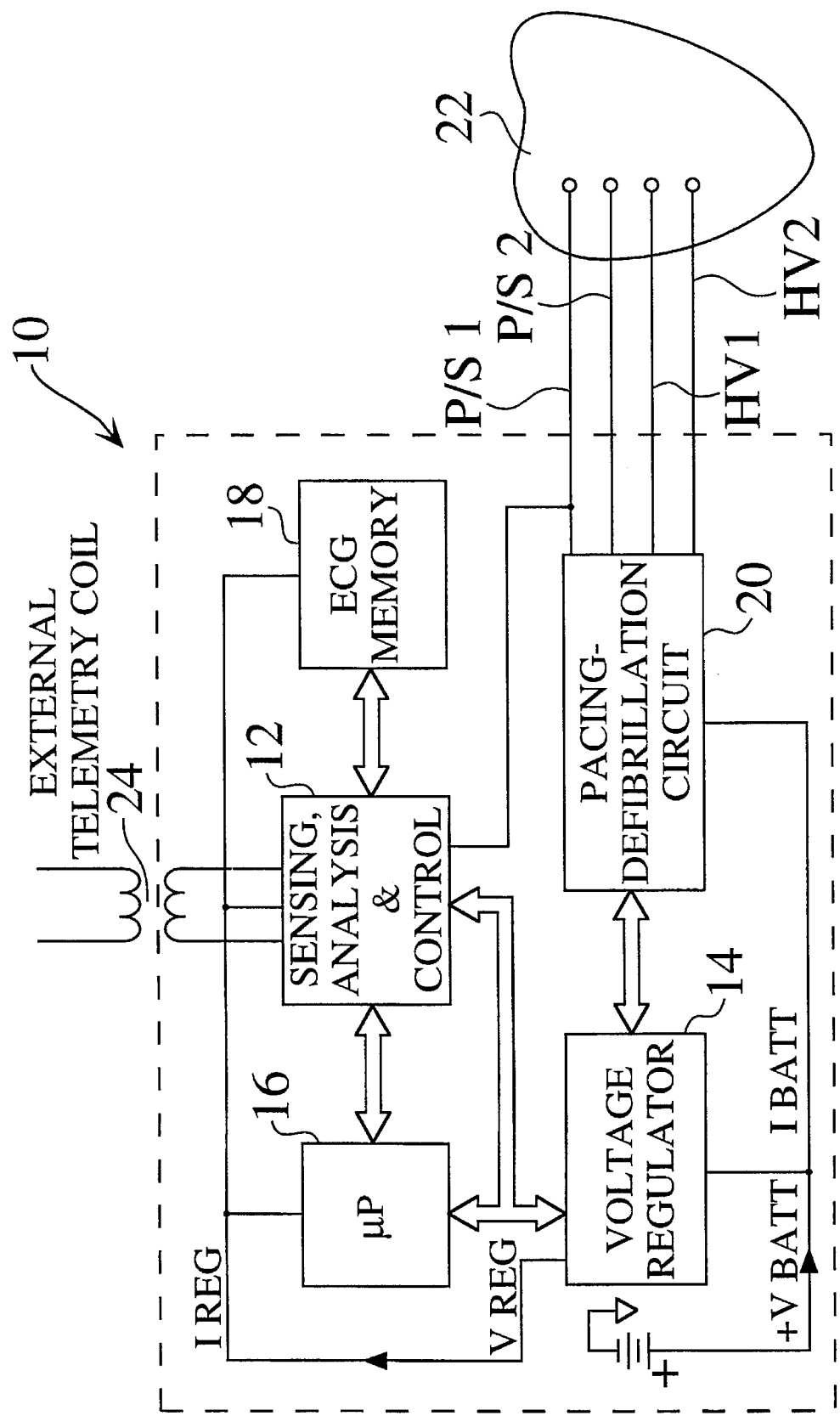
FIG. 1 is a block diagram illustrating the general organization of an implantable cardioverter/defibrillator.

FIG. 1 provides a block diagram showing the general organization of an implantable cardioverter/defibrillator (ICD) system 10. The ICD 10 includes sensing, analysis and control circuitry 12, a voltage regulator circuit 14 and a microprocessor 16. A static random access memory (RAM) 18 is used to store digitized ECG waveforms. External connections from a pacing-defibrillation circuitry 20 to the heart 22 are provided by two high voltage (HV) conductors HV1 and HV2, and a pair of pace/sense conductors P/S1 and P/S2 through which millivolt level ECG signals are sensed and which also carry pacing pulses to the heart 22.

Telemetry to and from an external programmer is carried via a coil-to-coil link 24. System software within the microprocessor 16 determines whether the ECG parameters indicate an arrhythmia and, if so, the appropriate therapy is initiated. The raw ECG data can also be stored in memory 18 for later retrieval, or it can be telemetered out of the system 10 in real time. Microprocessor 16 monitors the charge time of the HV capacitors in the pacing-defibrillation circuitry 20 to determine whether there has been any degradation in capacitor performance. The general operation of one exemplary embodiment of the system 10 is described in U.S. Pat. No. 5,111,816 to Pless et al., which is incorporated herein by reference in its entirety.

Figure 2:
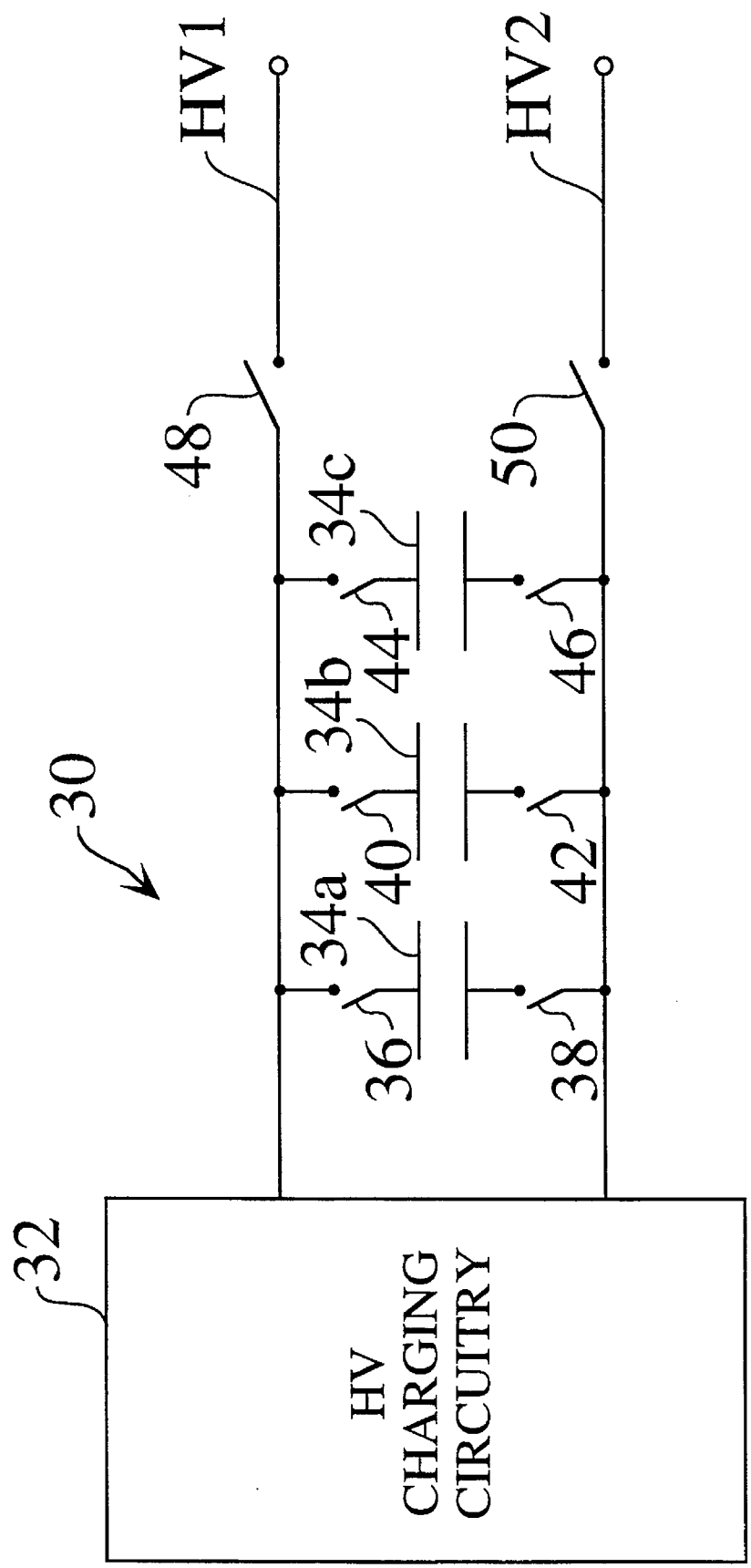
FIG. 2 is a schematic diagram of the high voltage output stage of the ICD of FIG. 1 in accordance with the invention.

FIG. 2 shows a schematic diagram of a HV output stage 30 which is a portion of the pacing-defibrillation circuitry 20. The output stage 30 includes HV charging circuitry 32 and three HV capacitors 34a, 34b and 34c. The output stage 30 further includes a switching matrix with a pair of switches used to selectively connect each of the capacitors to the HV charging circuitry 32. Switches 36 and 38 are coupled to either side of capacitor 34a, switches 40 and 42 are coupled to either side of capacitor 34b and switches 44 and 46 are coupled to either side of capacitor 34c. In many embodiments, it is not actually necessary to have switches on both sides of each capacitor. For example, in FIG. 2, switches 38, 42 and 46 could be eliminated (replaced by a conductor) and the capacitors 34a, 34b and 34c could be switched in and out of connection with the charging circuit by switches 36, 40 and 44 which are connected to common terminals of the capacitors, for example the anode terminals. An additional pair of switches 48, 50 are respectively coupled between the capacitors and the two HV conductors HV1 and HV2. Each of the switches in the output stage 30 is under control of the microprocessor 16. The voltage on each of the capacitors 34a–34c can be monitored along lines 35a–35c, respectively. It is noted that three capacitors have been shown for purposes of illustration but that the invention may be practiced with two or more capacitors coupled in parallel. It is further noted that each HV capacitor may actually comprise two or more series capacitors or a plurality of capacitor layers as is necessary to achieve the needed high voltage capability. It is also noted that for purposes of illustration a monophasic output stage is shown. It will be understood by those skilled in the art that an H-bridge circuit could be used to provide the capability to provide a biphasic output.

In operation, the implanting physician will determine the patient's DFT at the time of implant. If the required energy can be delivered with fewer than all of the capacitors, for example in this case two of the three capacitors, then ICD 10 will be programmed through telemetry coil 24 to close switches 36 and 38 to bring capacitor 34a into the circuit and switches 40 and 42 to bring capacitor 34b into the circuit. Switches 44 and 46 would remain open at this time. It may be preferable, depending on the switches used, to have all of the switches remain open until it is time to charge the capacitors and then to close the appropriate switches under control of microprocessor 16. This may be preferred because retaining the switches in a constantly closed position may require a certain amount of battery power. By charging only two and not all three of the capacitors, the charge time is significantly reduced while still providing sufficient energy delivery for defibrillation. This in turn will increase the likelihood of success of the defibrillation shock. If at some future time the patient's physician determines that the patient's DFT has changed or a higher energy defibrillation shock is desired for some other reason, then the ICD 10 may be reprogrammed, again via telemetry coil 24, to utilize all three of the capacitors in delivering the defibrillation shocks. While this will increase the HV capacitor charge time, it does provide the additional desired energy delivery capability.

In another embodiment of the invention, the microprocessor is programmed to automatically switch in additional ones of the back-up capacitors if defibrillation is not achieved with fewer capacitors in the circuit. This can be done at the same voltage of an initial defibrillation shock which has failed or may be implemented after a shock at the highest programmed voltage has failed.

In another use of the invention, fewer than all of the parallel connected capacitors are again used. The charge time for the capacitors is monitored by the microprocessor 16 during therapy delivery or during periodic charging to "reform" the capacitors if needed or during a periodic self-diagnostic charging. If the charge time of the capacitors is determined to be abnormally longer than expected, such as may be caused by a leakage current within the capacitor, then the unused capacitor may be used to replace the capacitor exhibiting degraded performance. With the self-diagnostics test or during a reforming charging procedure, each capacitor can be individually charged and have its charge time monitored. Where the long charge time is detected as part of capacitor charging for therapy delivery, the individual capacitors will then have to be individually tested as it would otherwise be impossible to tell which capacitor had degraded. Each of these tests is performed under control of the microprocessor.

Information regarding the switching out of a degraded capacitor is stored in device diagnostics such that the continued viability of the individual ICD unit can be determined by the patient's physician at his or her next follow-up appointment. It may be determined that the ICD is adequately functional and should remain in use. It may alternatively be determined that due to a combination of factors, including remaining battery life, that the unit should be replaced.

Although the invention is described herein with reference to the preferred embodiment, one skilled in the art will readily appreciate that other applications may be substituted for those set forth herein without departing from the spirit and scope of the present invention. For example, different size capacitor could be used to allow for a certain amount of fine tuning of the selected energy delivery. Accordingly, the invention should only be limited by the claims included below.

The invention claimed is:

1. An implantable defibrillator including a high voltage output stage comprising:

high voltage charging circuitry;

a plurality of high voltage capacitors coupled in parallel;

a switching matrix coupled between said charging circuit and said capacitors to selectively couple at least one of said capacitors to said charging circuit;

means coupled to said capacitors for monitoring the charge time for each of said capacitors to determine the performance of each of said capacitors;

means coupled to said monitoring means for determining from said charge time whether a given capacitor exhibiting degraded performance should be replaced; and a pair of output terminals coupled to said at least one of said capacitors.

2. The implantable defibrillator of claim 1 wherein each of said capacitors includes first and second capacitor terminals coupled to opposite sides of said capacitor and wherein said switching matrix includes at least one switch for each of said capacitors with at least one of said switches coupled between said first capacitor terminal of each of said capacitors and said charging circuitry.

3. The implantable defibrillator of claim 2, wherein said means for determining further includes means to isolate a capacitor exhibiting degraded performance from said output stage by opening said at least one switch coupled to said capacitor exhibiting degraded performance.

4. A method for using an implantable defibrillator having a plurality of selectively switchable parallel connected high voltage output capacitors, said method comprising the steps of:

using a selected number of said plurality of capacitors less than all of said plurality for delivery of defibrillation shocks;

monitoring the charge time for said selected capacitors to determine the performance of each of said selected capacitors; and replacing a selected capacitor exhibiting degraded performance with one of said capacitors which was not in said selected number of capacitors.

* * * * *